(12) United States Patent
Malonek et al.

(10) Patent No.: US 7,412,289 B2
(45) Date of Patent: Aug. 12, 2008

(54) MULTI-ELECTRODE LEAD

(75) Inventors: Dov Malonek, Tivon (IL); Nissim Darvish, Haifa (IL); Judith Kornfeld, Haifa (IL)

(73) Assignee: Impulse Dynamics (Israel) Ltd., Tirat Hacarmel (IL)

( * ) Notice: Subject to any disclaimer, the term of this patent is extended or adjusted under 35 U.S.C. 154(b) by 0 days.

(21) Appl. No.: 09/849,637

(22) Filed: May 4, 2001

(65) Prior Publication Data

US 2002/0055764 A1 May 9, 2002

Related U.S. Application Data

(63) Continuation of application No. PCT/IL99/00596, filed on Nov. 4, 1999.

(30) Foreign Application Priority Data

Nov. 5, 1998 (IL) .................................. 126905

(51) Int. Cl.
*A61N 1/05* (2006.01)
(52) U.S. Cl. ..................... 607/119; 607/122
(58) Field of Classification Search ............. 607/119, 607/122, 4, 5, 9, 14
See application file for complete search history.

(56) References Cited

U.S. PATENT DOCUMENTS

| | | | |
|---|---|---|---|
| 4,484,586 A | 11/1984 | McMickle et al. | |
| 4,602,637 A | 7/1986 | Elmqvist et al. | |
| 4,603,704 A * | 8/1986 | Mund et al. | 607/116 |
| 4,611,604 A * | 9/1986 | Botvidsson et al. | 607/122 |
| 4,762,136 A | 8/1988 | Baker, Jr. | |
| 4,848,352 A | 7/1989 | Pohndorf et al. | |
| 5,083,564 A * | 1/1992 | Scherlag | 607/9 |
| 5,205,284 A | 4/1993 | Freeman | |
| 5,246,014 A | 9/1993 | Williams et al. | |
| 5,265,623 A * | 11/1993 | Kroll et al. | 607/122 |
| 5,318,572 A | 6/1994 | Helland et al. | |
| 5,385,579 A | 1/1995 | Helland | |
| 5,405,375 A * | 4/1995 | Ayers et al. | 607/122 |
| 5,456,706 A * | 10/1995 | Pless et al. | 607/122 |
| 5,534,022 A * | 7/1996 | Hoffmann et al. | 607/122 |
| 5,545,205 A | 8/1996 | Schulte et al. | |
| 5,571,158 A | 11/1996 | Boiz et al. | |
| 5,649,966 A * | 7/1997 | Noren et al. | 607/4 |
| 5,654,030 A | 8/1997 | Munshi et al. | |
| 5,683,445 A * | 11/1997 | Swoyer | 607/119 |
| 5,683,447 A | 11/1997 | Bush et al. | |
| 5,711,298 A | 1/1998 | Littmann et al. | |
| 5,769,881 A | 6/1998 | Schroeppel et al. | |
| 5,814,079 A * | 9/1998 | Kieval | 607/4 |
| 5,824,016 A * | 10/1998 | Ekwall | 607/121 |
| 5,824,030 A * | 10/1998 | Yang et al. | 607/122 |

(Continued)

FOREIGN PATENT DOCUMENTS

WO    WO 97/25098    7/1997

*Primary Examiner*—George R Evanisko
(74) *Attorney, Agent, or Firm*—WolfBlock LLP; William H. Dippert

(57) ABSTRACT

This invention is a lead (10) for modifying the activity of a tissue, particularly the heart. Electrodes are provided for performing sensing (15*p*) (15*d*), and/or signal delivery (16*p*) (16*d*) functions. A control unit controls the parameters of the electric field provided by signal delivery electrodes to prevent the generation of a propagation action potential in the tissue.

30 Claims, 9 Drawing Sheets

U.S. PATENT DOCUMENTS 5,957,842 A * 9/1999 Littmann et al. ............ 607/122
6,254,610 B1 7/2001 Darvish et al.
6,348,045 B1 2/2002 Malonek et al.
6,463,324 B1 * 10/2002 Ben-Haim et al. ............ 607/9

* cited by examiner

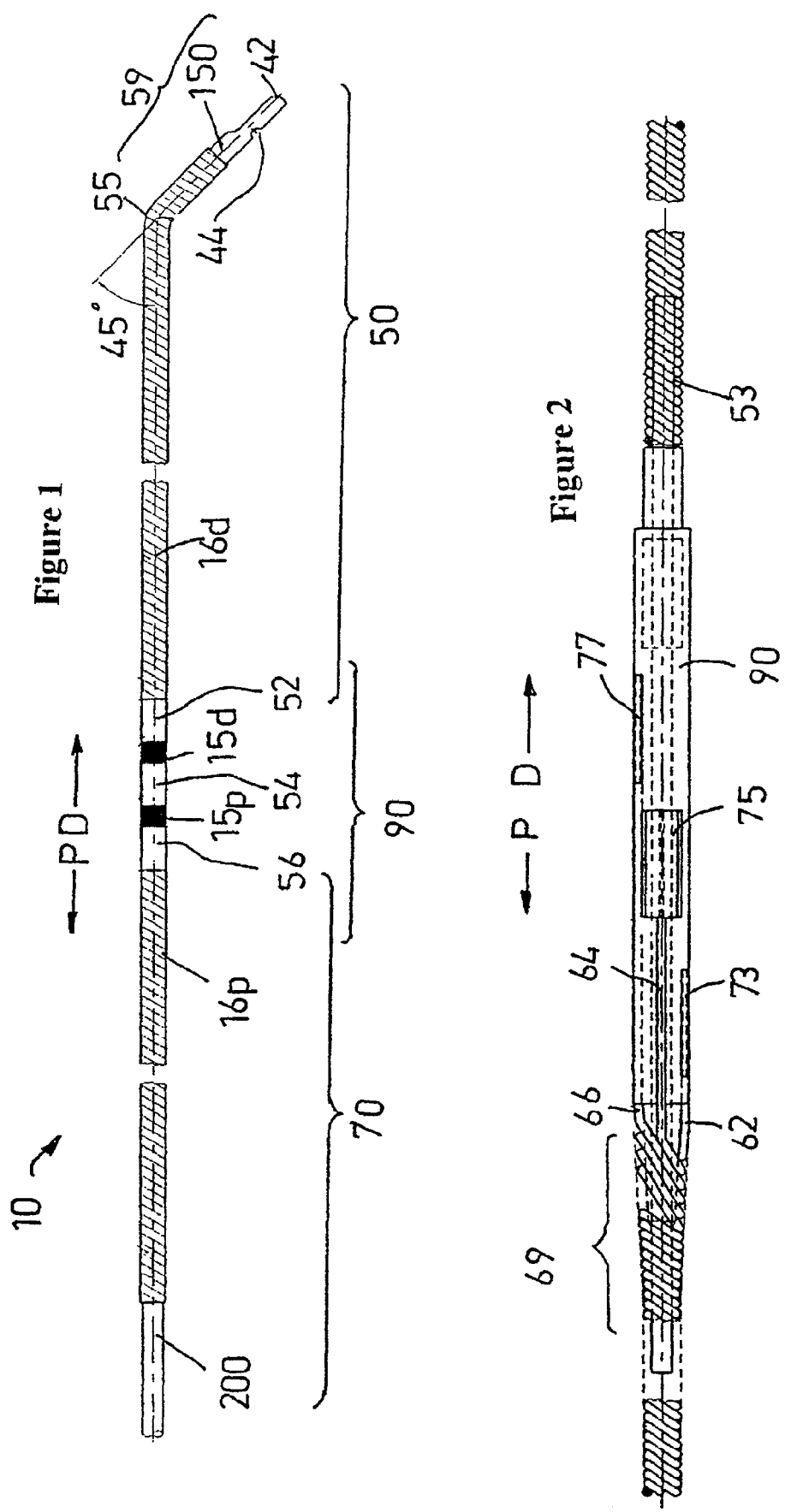

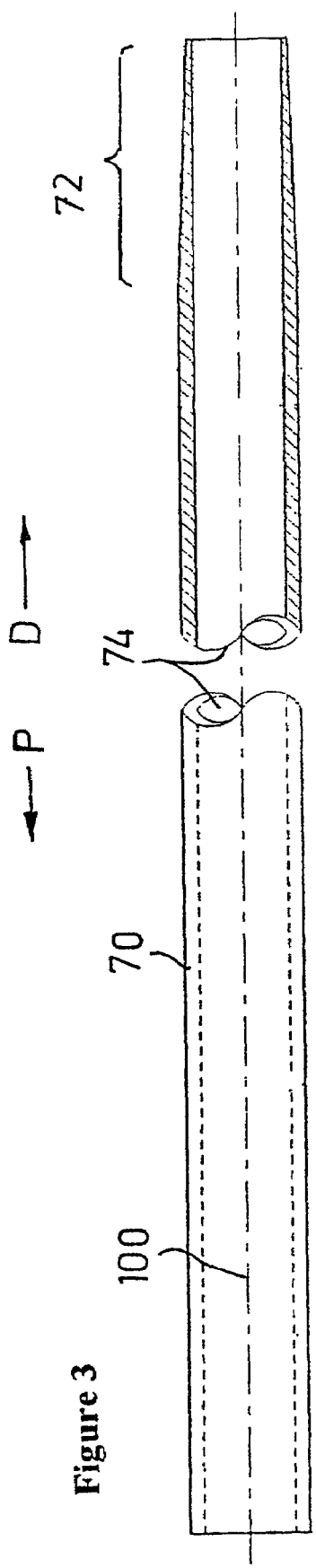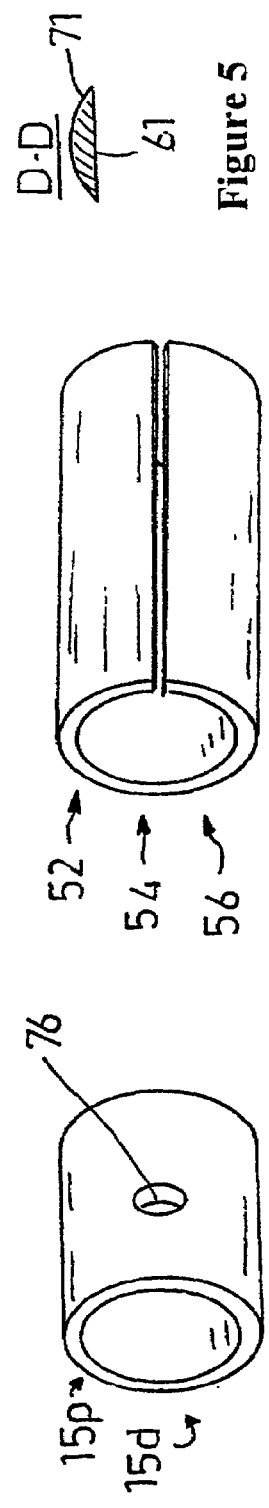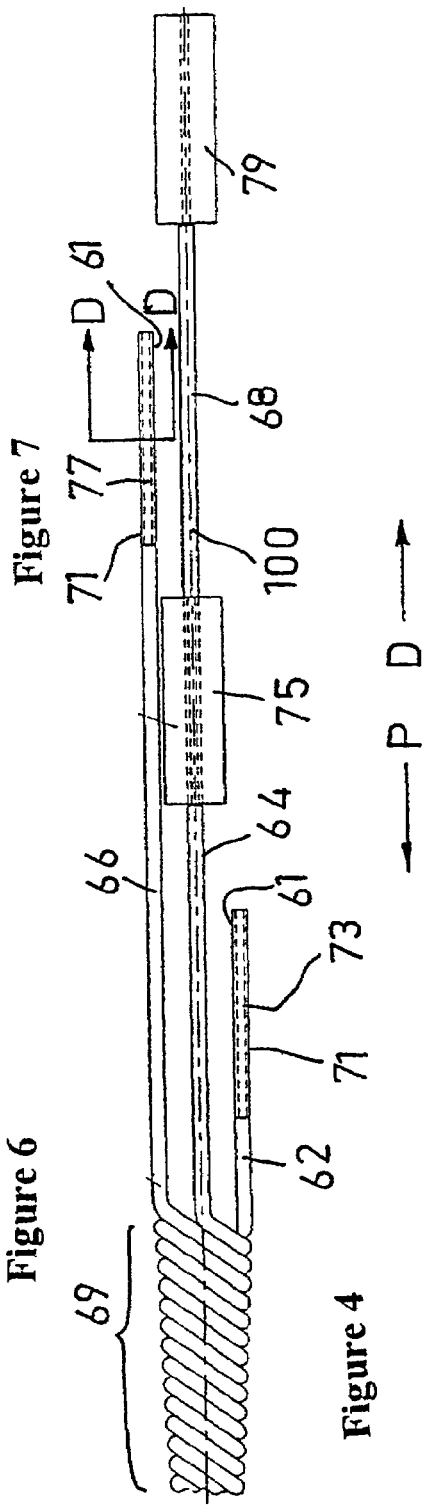

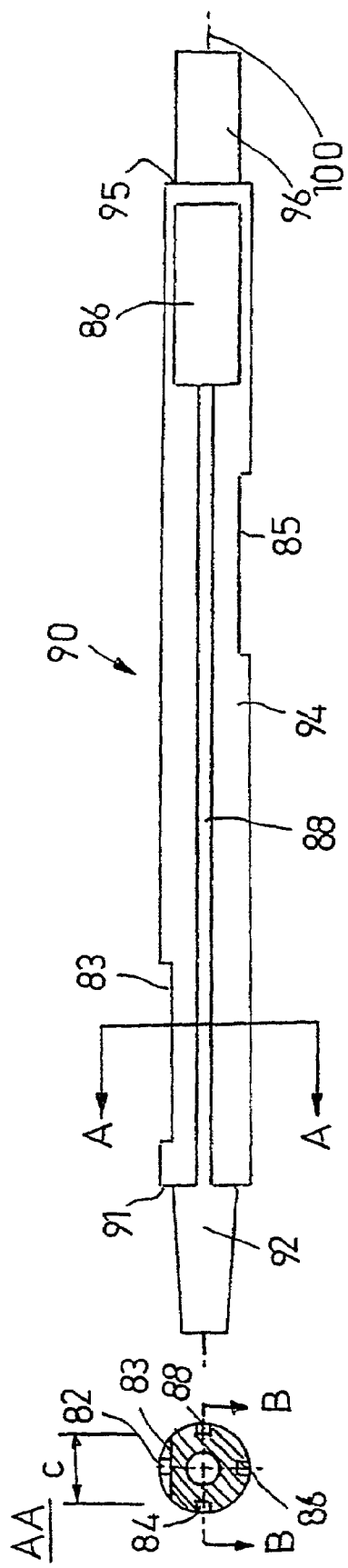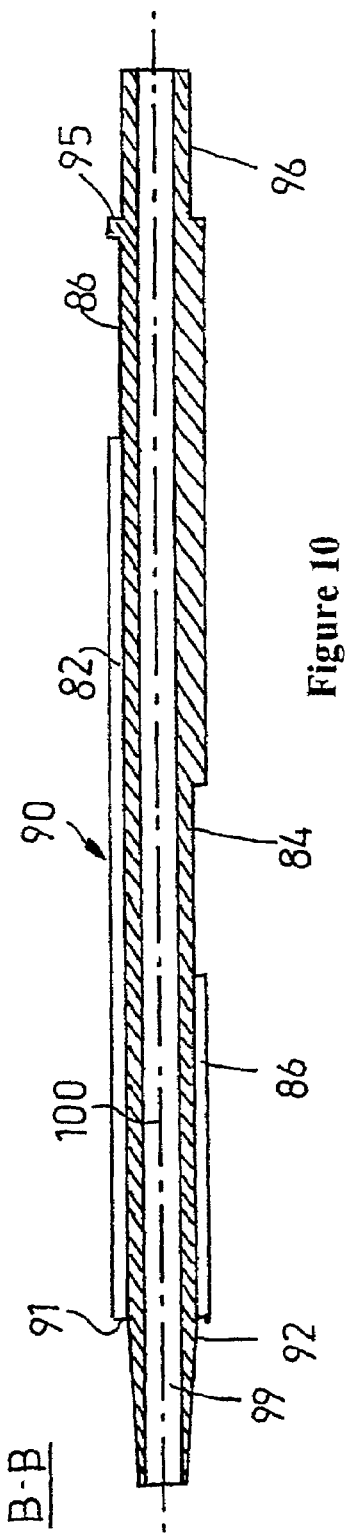
Figure 8
Figure 9
Figure 10

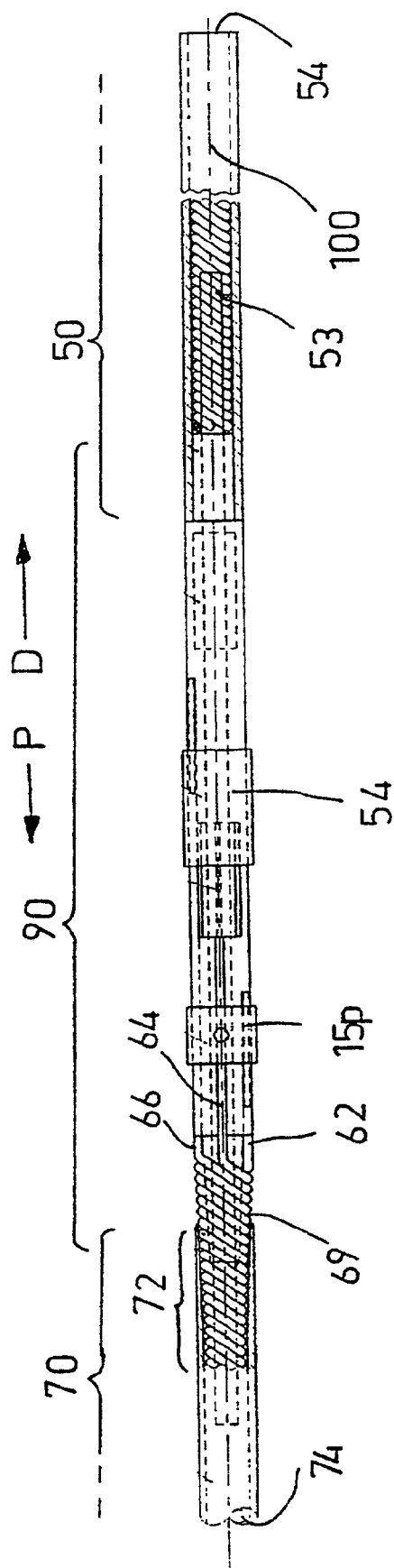
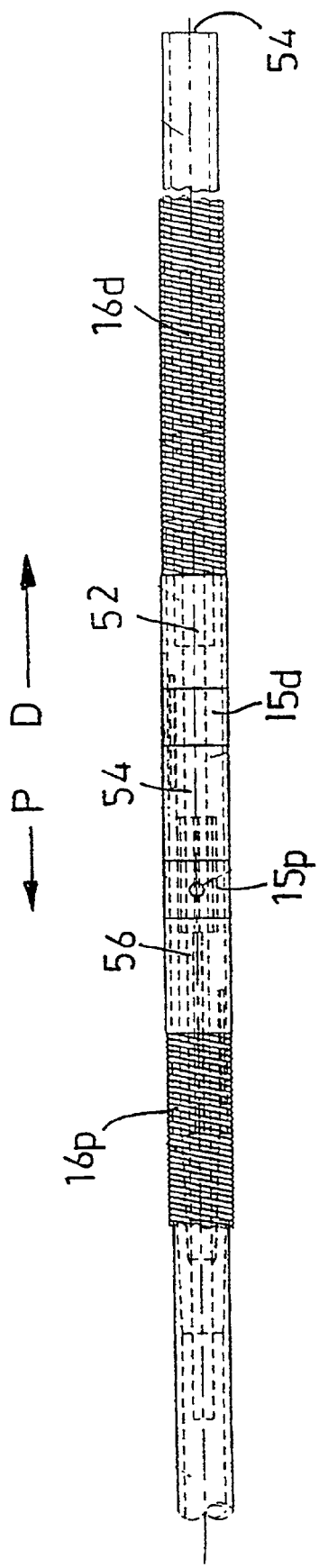
Figure 11
Figure 12

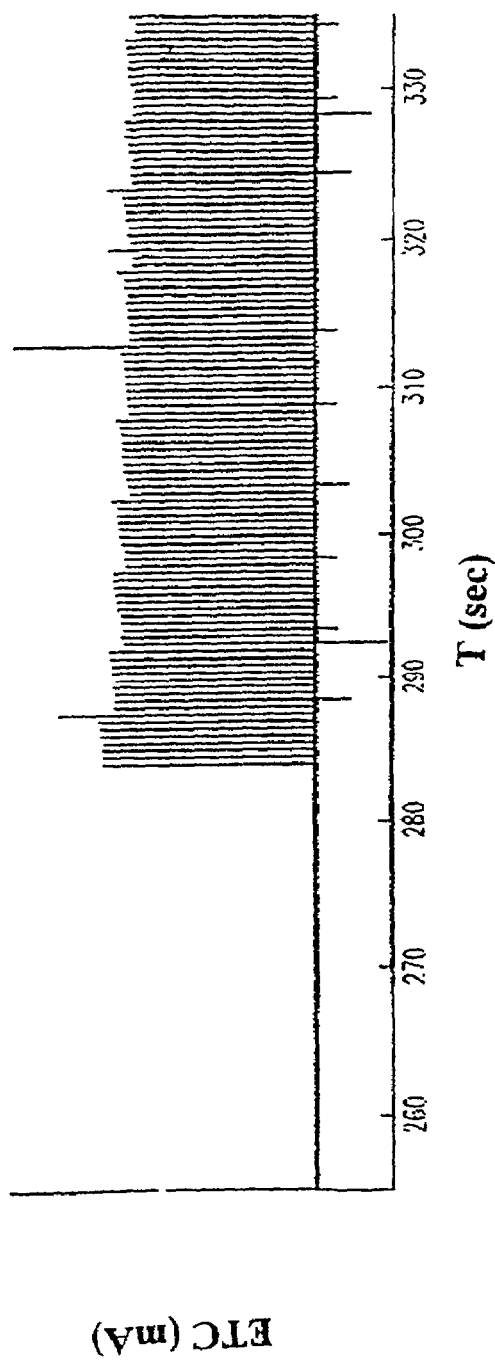
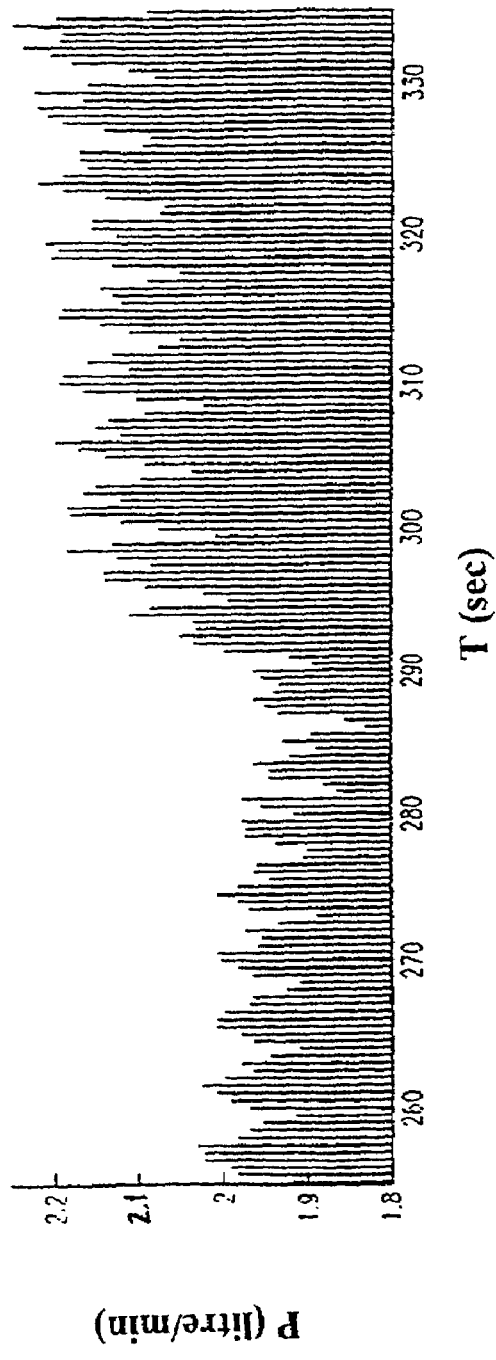

MULTI-ELECTRODE LEAD

This application is a continuation of international application number PCTIL99/00596, filed 4 Nov. 1999.

TECHNICAL FIELD

This invention relates to a lead having one or more electrodes for applying a non-excitatory signal to at least a portion of a tissue, and in particular to the cardiac muscle tissue, at times that are synchronized with the heart electrical activity.

BACKGROUND OF THE INVENTION

It is known in the art to apply cardiac leads employing electrodes that transmit electrical signals for three major purposes: mapping, pacing and defibrillating. Each lead type was designed to meet the electrical and mechanical requirements imposed by its intended use and location of operation.

In the beating heart, the intrinsic electrical activity propagates along the HIS-Purkinje intrinsic conductance pathways and between neighboring muscular regions. Changes in localized electrical activity in the form of cellular depolarization cause local contraction of that muscular region. The depolarization wave arrives to different cardiac locations at different delays from the intrinsic or artificial pacemaker. In order to synchronize the delivery of contractility modulating electrical signal to each of the localized cardiac regions, the precise timing of localized depolarization at that same location is needed. An example for such contractility-enhancing signal is the non-excitatory signal described in WO 97/25098, the description of which is incorporated herein by reference.

The catheter known in the art to be used for electro-physiological (EP) mapping of the cardiac muscle generally senses the localized cardiac electrical activity at the point of contact between the electrode and the muscle to detect regions of abnormal activity. Generally, a small surface area characterizes the electrodes of said catheter to achieve reliable sensing. Among the different catheters, some are used for mapping the endocardial walls of the cardiac chambers; they are large in diameter, generally 2.5-3.0 mm, and have only a few electrodes at the tip of the catheter, whose position can be controlled by external means. Different parts of the cardiac chamber (atrium or ventricle) wall can be accessed sequentially, and their localized electrical activity mapped. Other mapping catheters, which are used to access the epicardial wall, via the coronary venous system, are very thin, generally less than 1 mm in diameter, and therefore enables access to the small branches of the vasculature and employ small, multiple electrodes distributed along the length of the catheter. Generally, the vessel's diameter decreases toward the branches, from the ostium of the coronary sinus, via the great cardiac vein to less than 30 μm at the venules.

The art deals, e.g., in U.S. Pat. No. 5,711,298, with the high resolution mapping of localized cardiac electrical activity through the coronary vasculature, and employs catheters with a plurality of sensing electrodes distributed along it, or guidewire stem with inter-electrode distance of less than 2 mm. The shaft of the catheter is formed of a plurality of insulated conductors, braided or wound into an elongated tubular shape with a central lumen and an external sleeve covering the entire shaft. The diameter of the shaft is preferably less than 0.75 mm. These electrodes are small, designed for sensing of electrical activity and they are not designed for the delivery of electrical energy to the tissue. Similarly, the shaft of the catheter is not designed for long term implant and high fatigue life.

Prior art methods for the delivery of electrical energy into the cardiac muscle include pacing leads and defibrillator leads. Both types of leads do not provide means for efficient energy delivery at multiple locations nor provide non-excitatory electric fields at localized locations in the cardiac chamber. The unipolar pacing lead has a small signal delivery tip (1-10 mm$^2$) through which the electrical energy is sensed from, and delivered into, a single localized region of the tissue generating a propagating action potential. The bipolar pacing lead has an additional ring electrode that enables localized sensing and signal delivery. However, similar to the unipolar lead, these electrodes and leads are designed for energy delivery and sensing from a single and small localized region of the cardiac muscle. The position of the lead is normally in one of the cardiac chambers, although some pacing leads can be used for cardiac stimulation through the coronary sinus or cardiac veins. There are also other forms of pacing leads, for example epicardial pacing leads that are attached to the epicardial wall of the heart, capable of performing similar functions. A typical pacing pulse is a sharp, narrow electrical pulse with a 0.1 to 1.5 msec duration, a total discharge of 0.1-50 μC and an energy of about 100 μJ. It does not require that the electric capacitance of the electrode be high, because of the short duration of the signal, and a value of less than 100 μF, which is the value used in the art, is sufficient. It is also required that the electrode will have a short recovery time to enable it to act as a sensor within a few milliseconds after delivering the signal. The electric field applied, through high impedance, is local and generally low. U.S. Pat. No. 4,848,352 discloses a method and device for cardiac pacing and sensing which uses a plurality of electrodes carried by a lead.

The defibrillator lead and electrodes are designed for the delivery of a small consecutive number of high energy pulses to the cardiac muscle upon demand. This energy delivery is to the whole mass of the chamber, and thus it is not localized. The defibrillator electrode is not used for the sensing of the localized electrical activity, and separate sensing electrodes are needed. The additional sensing electrode(s) are situated on the same defibrillator lead, or on a pacing lead that is positioned elsewhere in the heart. Both methods of electrical signal sensing are not adequate for signal detection at the vicinity of a defibrillator electrode. U.S. Pat. No. 5,545,205 discloses a unitary intravascular defibrillating lead which is part of an apparatus which includes a cardioversion circuit, and carries a distal and proximal spring electrode, displaced at such distance from one another that defibrillating shock is affected through a field including the interventricular septum and left ventricular free wall.

The use of a multi-chamber lead or catheter through the GCV for pacing, whether combined or not combined with non-excitatory signal delivery, has not been described in the art.

What has been needed is a method and system for the precise delivery of multiple electrical signals to a plurality of locations on the cardiac muscle, each of which is synchronized, to the locally sensed intrinsic electrical activity.

The timing and characteristics of an electrical field that modifies the contractility of the heart and the sensing required for controlling the delivery of the signal required, are entirely different from any signal applied to the heart for pacing or defibrillating. Subsequently, there is no lead known in the field that fulfills the combination of requirements of a lead employing electrodes that deliver a non-excitatory signal in the appropriate timing and location. Such a lead and such electrodes are the objects of this invention.

This invention has the purpose of providing a device, in particular a multi-electrode lead, to deliver a non-excitatory signal.

It is another purpose of this invention to provide a device to deliver such a signal synchronized with the local intrinsic excitatory signal of the heart.

It is another purpose of this invention to provide a device that is sufficiently thin as to be inserted transvenously into the distal veins of the Venous system of the heart to deliver such a signal to specific locations of the cardiac muscle.

It is another aim of the present invention to provide a lead adapted for being implanted onto the epicardial surface of the heart using any suitable method of implantation.

It is a further purpose of this invention to provide a lead employing electrodes that are small in surface area to provide reliable local signal delivery and sensing, and at the same time, large enough to be able to deliver, through low impedance, electrical pulses whose energy is higher than that of the pacing pulses.

It is a further purpose of this invention to provide a lead employing electrodes that are small in surface area to provide reliable signal delivery and sensing at multiple locations.

It is a further purpose of this invention to provide a lead employing electrodes which have low impedance, deliver higher energy than pacing energy, but are still biostable for long term implantation.

It is a still further purpose of this invention to provide a lead employing electrodes that deliver a signal of duration determined by the duration of the refractory period.

It is yet another purpose of this invention to provide a lead, primarily intended for such non-excitatory stimulation though capable of performing pacing and defibrillating functions.

It is yet another purpose of this invention to provide a lead, primarily intended for such non-excitatory stimulation though capable of performing pacing and defibrillating functions separately or in combination.

It is still a further object of tie invention to provide a method for applying non-excitatory stimuli to an organ or body cavity.

Other purposes and advantages of the invention will appear as the description proceeds.

SUMMARY OF THE INVENTION

The invention is directed to a device for sensing or detecting the localized activity from within, and delivering non-excitatory electrical signals to, a patient's heart at a single or multiple locations therein. The term "activity" includes herein any suitable mechanical, electrical, or chemical activity that gives an indication of excitation of the tissue. The device, typically a lead, can be positioned at different branches of the coronary vasculature, or alternatively on the epicardial layer of the heart, and is suitable for delivering electrical energy to multiple locations in the heart, in synchrony with the local intrinsic activity at each position. This synchronous delivery of the signal is essential for local delivery of a safe and reliable non-excitatory signal to the cardiac muscle. Similarly, the invention is likewise directed to a device performing similar functions in other organs, tissues, vessels and cavities of the body.

Thus, in one aspect, the invention is directed to a lead for modifying the activity of a tissue, particularly the heart, or of a portion thereof, comprising signal delivery electrodes and sensing electrodes, said signal delivery electrodes being suitable to apply to said tissue, or portion thereof a non-excitatory electric field of a magnitude, shape, duty cycle, phase, frequency and duration suitable to obtain the desired change, and said sensing electrodes being suitable to sense the activity of the tissue or portion thereof, and to deliver a signal related to said sensed activity to a control unit, so that said field is applied by said signal delivery electrodes at a time such as to be unable to generate a propagating action potential.

The lead of the present invention is a device for chronic implants or for acute therapy which comprises in one embodiment at least one pair of electrodes in close proximity to one another, the electrodes typically being a signal delivery electrode and a sensing electrode, wherein each energy delivery electrode has an impedance in the range 50-500 Ohm. By "close proximity" is meant to indicate that the electrodes are positioned at a short distance from one another, e.g., up to about 10 mm.

In some embodiments, the lead is typically comprised of a plurality of electrode pairs, each pair consisting of a sensing electrode in close proximity with a signal delivery electrode. The actual distance corresponding to this "close proximity" is of great importance since the electrodes have to be close enough together to detect only the appropriate corresponding signal of the localized area in which it is desired to change the activity thereof. At the same time, the electrodes should not be so close so as to interfere with each other's electrical activity, such that the signal delivery electrode nearest to sensing electrode provides an electric field that corresponds with the signal provided by the corresponding sensing electrode. The sensing electrodes are preferably in the form of rings or pairs of rings, but may also be in any other suitable form including coils and half rings, for example. The sensing electrodes are typically made from any one of the following materials, for example: (a) Titanium plus Iridium oxide coating; (b) Titanium plus titanium nitride coating; (c) Platinum Iridium plus Iridium oxide coating; (d) Platinum Iridium plus titanium nitride coating; (e) Platinum Iridium plus sintered platinum coating; (f) Titanium, (g) Platinum Iridium, (h) Pyrolitic carbon; or any other conductive material having suitable biostable and biocompatible characteristics and having suitable capacitance.

The electrodes are spaced along the lead so as to occupy the length of the coronary sinus and/or the cardiac veins down to their thinnest branches. The thinner the electrodes, the greater the distance they can reach: e.g. electrodes having a 1 mm diameter can be inserted into the vasculature to a distance shorter than that of electrodes having a diameter of 0.5 mm. Thus the electrodes should be spaced along the lead such as preferably occupy a lead length from 20 to 150 mm, e.g. 100 mm. The overall surface of each signal delivery electrode should be comprised between 30 and 250 square mm, and the total surface of all the signal delivery electrodes should be comprised between 120 and 1000 square mm. Preferably, the signal delivery electrodes are made from a conductive wire having a diameter comprised between 0.05 and 0.125 mm, e.g., 0.125 mm. This conductive wire is preferably made from any one of the following materials, for example: (a) Titanium plus Iridium oxide coating; (b) Titanium plus titanium nitride coating; (c) Platinum Iridium plus Iridium oxide coating; (d) Platinum Iridium plus titanium nitride coating; (e) Platinum Iridium plus sintered platinum coating; (f) Pyrolitic carbon; or any other conductive material having suitable biostable and biocompatible characteristics and having suitable capacitance. In the embodiment illustrated, the electrodes are formed by coils, but other constructions (e.g. mesh of wires) are possible.

In embodiments particularly adapted for implantation on the epicardial layer of a tissue such as the heart, the lead may comprise one or a plurality of electrode units at the distal end thereof, each electrode unit typically comprising at least one signal delivery electrode and two sensing electrodes in close proximity thereto. Each electrode head may be spatially displaced with the respect to the other heads such as to provide a desired effect on a relatively large area of the tissue. The electrode units are connected to suitable connectors at the proximal end of the lead via suitable conductors carried by the lead. The lead may be connected to a suitable control unit implanted inside the body or located outside the body.

In other embodiments, the lead may comprise a single electrode to be used for performing the sensing and the signal delivery functions, since these are not simultaneously required, and the time interval between sensing functions is typically greater than the duration of the delivery signal after each sensing. Similarly, the lead may comprise a plurality of unitary electrodes, each of which is capable of performing the sensing and the signal delivery functions.

In yet other embodiments, at least one such unitary electrode may be comprised in a lead together with at least one sensing electrode and/or at least one signal delivery electrode.

BRIEF DESCRIPTION OF THE DRAWINGS

In the drawings:

FIG. 1 illustrates in side view the main elements of the preferred embodiment of the present invention.

FIG. 2 illustrates in side view the arrangement of conductors in relation to the terminal support member of the embodiment of FIG. 1.

FIG. 3 illustrates in partially sectioned and fragmented side view the proximal carrier shaft of the embodiment of FIG. 1.

FIG. 4 illustrates in side view the distal arrangement of the proximal conductors of FIG. 2.

FIG. 5 shows in transverse cross-sectional view a terminal of FIG. 4 along D-D.

FIG. 6 illustrates in perspective view a typical sensing electrode of the embodiment of FIG. 1.

FIG. 7 illustrates in perspective view a typical spacer between adjacent electrodes of the embodiment of FIG. 1.

FIG. 8 illustrates in top view the terminal support member of the embodiment of FIGS. 1 and 2.

FIG. 9 illustrates in transverse cross-sectional view the terminal support member of the embodiment of FIG. 8 along A-A.

FIG. 10 illustrates in longitudinal cross-sectional view the terminal support member of the embodiment of FIG. 9 along B-B.

FIG. 11 illustrates in side view the embodiment of FIG. 2, further comprising proximal and distal carrier shaft portions and a spacer, illustrating the mounting of a sensing electrode.

FIG. 12 illustrates in side view the arrangement of sensing and signal delivery electrodes in relation to the support shaft of the embodiment of FIG. 1.

FIG. 15b illustrates in transverse cross-sectional view the sensing electrodes of the embodiment of FIGS. 13 and 15a.

FIGS. 22(a) and 22(b) illustrates test results regarding improvement in pulsatile flow through the heart of an animal subject using one embodiment of the invention.

DISCLOSURE OF INVENTION

Figure 13:
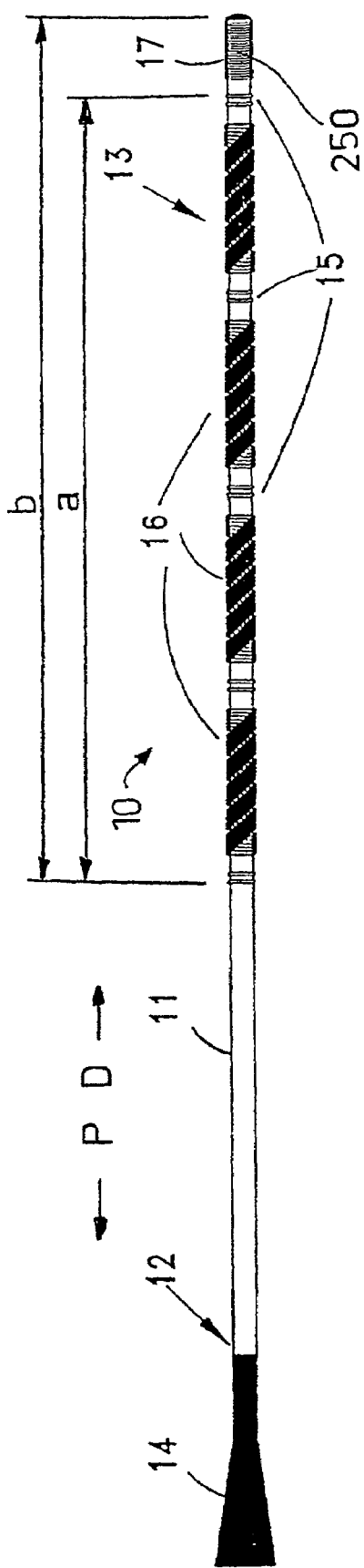
FIG. 13 illustrates in side view the main elements of the second embodiment of the present invention.

The present invention is defined by the claims, the contents of which are to be read as included within the disclosure of the specification, and will now be described by way of example with reference to the accompanying Figures.

In the present specification, the term "distal" refers to a direction towards and into the tissue or portion thereof in which it is desired to perform a change in its activity, while the term "proximal" refers to a direction away from the said tissue (and typically, but not necessarily towards the control unit).

In the present invention, the term "tissue" relates to any organ or system or part thereof in the body, in particular the heart, in which it is desired to change the activity thereof.

The term "activity" includes herein any suitable mechanical, electrical, or chemical activity that gives an indication of excitation of the tissue.

In the present invention the term "lead" relates to any type of device that may be inserted into, or otherwise positioned with respect to, a cavity, duct, organ, tissue or vessel of a human body while maintaining another end of the device connected to a suitable control means, which may be either implanted in the body or positioned external thereto, for enabling communication (fluid, electrical, optical or other) to be established between the control unit and a particular area within the body. The term "lead" is thus taken herein to also include catheters and other such medical devices, whether or not they incorporate one or more lumens for delivering and/or extracting fluids, and without reference to the intended period of implantation of the device within the body. The lead according to the present invention may be for the delivery of acute therapy or chronic therapy.

The term "multi-electrode" is also taken herein to include a single electrode having the capability of performing multiple functions, for example sensing and signal delivery.

The present invention is directed at lead for modifying the activity of at least a portion of a tissue, the lead comprising:

electrode means adapted for sensing activity of said at least portion of a tissue and providing a signal characteristic of said activity, said electrode means also adapted for selectively delivering a suitable non-excitatory electric field to said at least portion of tissue to achieve a desired change;

connection means operatively connected to said electrode means for enabling said electrode means to be operatively connected to a suitable control means.

Thus, the electrode means is capable of sensing activity within one or more specific localities in the tissue, and is also capable of delivering non-excitatory signals to one or more specific targets within the tissue.

The said electrode means may comprises at least one unitary electrode, each said unitary electrode being adapted for sensing the activity of said at least a portion of tissue and providing to said control means a signal characteristic of said activity non-simultaneously with respect to the selective generation of said suitable non-excitatory electric field to said at least a portion of a tissue by same said at least one unitary electrode.

Additionally or alternatively, said electrode means comprises at least one sensing electrode adapted for sensing said activity of said at least a portion of a tissue and for providing a signal characteristic of said activity, and wherein said electrode means further comprises at least one signal delivery electrode adapted for selectively delivering a suitable non-excitatory electric field to said at least portion of a tissue to achieve a desired change therein.

Thus, in one embodiment of the present invention, the lead comprises:

- at least one electrode adapted for sensing activity of said at least portion of a tissue and providing a signal characteristic of said activity, said at least one electrode also adapted for selectively delivering a suitable non-excitatory electric field to said at least portion of tissue to achieve a desired change;
- connection means operatively connected to said at least one electrode for enabling said at least one electrode to be operatively connected to a suitable control means.

Further, in another embodiment of the invention, the lead comprises:

- at least one sensing electrode adapted for sensing the activity of said at least portion of a tissue and providing a signal characteristic of said activity; and
- at least one signal delivery electrode adapted for selectively delivering a suitable non-excitatory electric field to said at least portion of tissue to achieve a desired change;
- connection means operatively connected to said at least one sensing electrode and to said at least one signal delivery electrode for enabling said at least one sensing electrode and to said at least one signal delivery electrode, respectively, to be operatively connected to a suitable control means.

Such control means typically comprises a control unit characterised in being adapted for (I) selectively enabling a suitable non-excitatory electric field to be generated by said electrode means such as to provide the desired modification in the activity of said portion of tissue, and (II) for selectively not generating an electric field; according to at least one at least one characterising feature of said signal previously provided by said electrode means. Examples of such suitable control means are disclosed in co-pending application WO 97/25098, entitled "Electrical Muscle Controller", the contents of which are incorporated herein in their entirety.

Thus, said control means comprise means for receiving said signals from said sensing electrodes and means for determining on the basis thereof the parameters of the electrical field provided by each said signal delivery electrode and the sequencing thereof. Said parameters typically include at least one of:—the magnitude, shape duty cycle, phase, frequency and duration of said non-excitatory electric field. The control means typically comprises means for applying to said signal delivery electrodes a voltage and/or current required for performing an operation chosen from among providing non-excitatory stimuli to the heart or performing pacing or performing defibrillation. Further, the control means typically comprises means for generating a non-excitatory electric field having suitable parameters such as to provide the desired change in the activity of the tissue or part thereof.

In one application, each said electrode of said lead may be used for identifying the location thereof relative to the anatomical boundary between the atrium and the ventricle of the heart.

The present invention is thus directed at a lead comprising one or more electrodes adapted for providing sensing and energy delivery functions, typically, but not necessarily, carried on an elongate flexible shaft. The lead may comprise one or multiple sensing electrodes, and may also comprise one or multiple energy delivery electrodes on the same shaft as the sensing electrodes, wherein each signal delivery electrode is preferably situated in close proximity to one or more sensing electrodes.

The typical sequence of events for applying a non-excitatory signal to a region of the heart, for example is as follows. A localized intrinsic field signal (of duration in the order of a few milliseconds) is detected via the sensing electrodes. The non-excitatory field is provided by the signal delivery electrodes and lasts in the order of tens of milliseconds, usually between about 5 msec and about 100 msec. The next intrinsic localized signal typically appears about 500 msec to about 1000 msec after the previous sensed signal. There is therefore a large time interval between each successive signal received by the sensing electrodes, in comparison to the duration of the electric field provided by the signal delivery electrodes. This, plus the fact that the electric field is set up after the sensing signal has been received, enables one electrode to perform both functions of sensing the electrical activity of the tissue and of providing the non-excitatory electric field thereto. While the above example was directed at the heart as the target tissue, the situation with other organs and tissues, including particularly the urinary bladder and uterus, is similar. Thus, in alternative embodiments of the invention, one or more electrodes may each provide both the sensing and signal delivery functions.

Typically, the distal part of the lead comprises multiple sensing and signal delivery electrodes operatively connected via suitable conductors to suitable connecting means, such as typically a multi-pin connector or several connectors, comprised in the proximal part of the lead, for delivery of the signals of each energy delivery electrode as well as for receiving sensing signals from the sensing electrodes. In accordance with one embodiment of the invention the distance between each signal delivery electrode and a nearby sensing electrode (or electrodes) is between 1-10 mm, in the preferred embodiment about 2 mm, and in other embodiments typically about 5 mm. The short distance between each pair of adjacent sensing and signal delivery electrodes allows for accurate monitoring of local electrical activity at a site that is in proximity to the non-excitatory signal delivery site.

Typically, the proximal part of the lead comprises any suitable connection means including multi-pin connector, or several connectors, or implantable connectors such as IS1 connectors. In one embodiment the pair of sensing electrodes are connected to IS1 Bipolar connector, and the pair of signal delivery electrodes are connected to another IS1 Bipolar connector.

In one embodiment, the shaft of the lead comprises multiple conductors that transmit electrical signals from one end of the lead to the other. The distal part of the lead is to reside in small blood vessels the inner diameter of which is less than 1.5 mm, and including in some cases vessels whose inner diameter is less than 1 mm.

The capability of the lead to reside in small branches of the vasculature makes it possible to deliver localized non-excitatory signals to cardiac segments that can otherwise be reached only through major surgical intervention. Because of its small diameter, special care is taken to ensure that the most distal part of the lead be made of soft ribbon or elongated coil, such that vessel trauma is minimized during insertion.

In some embodiments, the lead of the present invention requires the use of a method for inserting it into the coronary veins by means of an external guiding device, such as a guide wire or a pre-shaped stylet, or guide sheath. In one embodiment of the invention, the lead has a central lumen in which a stiffening stylet may be inserted. The central lumen may be formed by coaxial winding of the conductors thus forming a central lumen. Alternatively, several lumens may be formed in the shaft body. The conductors are inserted into specifically designated lumens while one lumen is kept for the stylet insertion. In a different embodiment, the lead does not have a central lumen but rather an external guiding apparatus is attached to its shaft. The apparatus may be in the form of a ring that is attached to the tip of the lead. While positioning the lead in its final position, a guide wire is used for its navigation. The guide wire is directed to the desired position in the coronary vasculature. Later, the ring is slipped on the guide wire and the lead is pushed forward, guided to its final position by the guide wire. The guide wire is then retrieved. Preferably, and in the preferred invention, implantation is accomplished according to the methods disclosed in co-pending applications filed in the U.S. under U.S. application Ser. Nos. 09/351,726 and U.S. Ser. No. 09/317,589. respectively entitled "Catheter with Distal-End Engaging Means" and "A Device and Method for Dragging and Positioning a Member within a Duct in a Body", which are incorporated herein in their entirety be reference thereto.

In other embodiments of the invention, the lead may be surgically implanted onto a tissue such as the heart, on its epicardial surface. In such cases the lead itself may be affixed to the tissue using known methods including the use of a screw, suture or elastic mesh.

Preferably, and in the preferred embodiment, the signal delivery electrodes occupy a relative large portion of the shaft length and the inter-electrodes distance should be minimal. The total length of lead that is occupied by signal delivery electrodes is typically about 20-150 mm, preferably about 100 mm. The distance between adjacent pairs of signal delivery electrodes is typically 5-30 mm, preferably about 8-10 mm. The energy level and duration of the non-excitatory signal requires that the impedance of the signal delivery electrode be low, and its capacitance be high (of the order of 300 µF-3,000 µF). A high capacitance helps to maintain the biostability of the electrode by minimizing deterioration thereof due to the high energy output. The signal delivery electrodes are in the form of elongated coils the length of which is 10-40 mm, preferably about 20-25 mm in the preferred embodiment. Such dimensions allow for relatively localized application of the non-excitatory signals, while minimizing its impedance. Similarly, the usage of a porous coating for the signal delivery electrodes maximizes its capacitance, and thus increases the efficiency of energy delivery to the tissue and prevents cross-talk between signals.

Each sensing electrode is adapted for sensing tissue impedance, pressure, tension and/or electrical signal.

In one embodiment, the sensing electrode is typically in the form of a ring positioned around the shaft, its length being typically about 0.25-1.00 mm, in the preferred embodiment about 1.00 mm, and in other embodiments typically about 0.5 mm.

Each sensing unit is typically, situated between two signal delivery electrodes and comprises a single sensing electrode, or a pair of sensing electrodes that is used for bipolar sensing. In this embodiment, the distance between adjacent sensing electrodes of such a pair is typically is 0.5-2.5 mm, preferably about 1 mm.

In the preferred embodiment, the lead comprises a plurality of pairs of said electrodes, each said pair comprising a said delivery electrode and a said signal electrode in adjacent axial arrangement. In particular, said lead comprises two said pairs of electrodes, the sensing electrode of one said pair of electrodes being in adjacent axial arrangement with respect to the sensing electrode of the other said pair of electrodes.

In embodiments comprising sensing electrodes arranged in pairs, both sensing electrodes of any particular pair are preferably substantially identical, dimensionally as well as regarding the material from which they are made.

Optionally, in addition to the sensing electrodes placed in close proximity to the signal delivery electrodes, more electrodes may be carried by the lead, at any location thereon, the additional electrodes capable of performing sensing functions and/or pacing functions and/or defibrillation functions to enhance the sensing, pacing and defibrillation capabilities of the lead.

In another embodiment, the sensing electrode is flanked by a signal delivery electrode at only one side thereof. For example, the lead may comprise a sensing electrode at its distal end.

In yet another embodiment, the lead may include just a single electrode capable of performing the required sensing and delivery functions.

Preferably, and in the preferred embodiment, the energy delivery electrodes each have an impedance in the range of 50-500 Ω. For comparison, the impedance of typical pacing electrodes, as used in the known art, is in the range of several hundreds to about 3 KΩ. Defibrillator leads, on the other hand, typically comprise relatively long electrodes (typically about 50 mm) with low impedance (about 50 Ω), because of the need to deliver a high power to the whole mass of the heart (non-localized) in a short period of time. The impedance of the electrode is mainly dictated by its dimensions. The use of porous materials increases the capacitance and minimizes the low frequency impedance of the electrode.

Referring to the Figures, FIGS. 1 to 12 illustrate a preferred embodiment of the present invention. In this arrangement, and as illustrated in FIGS. 1 and 12 in particular, the device or lead, designated by the numeral (10), comprises a pair of signal delivery electrodes (16p), (16d) flanking a pair of sensing electrodes (15p), (15d) arranged on an elongate carrier shaft (200). Non-conducting spacers (52), (54) (56) separate and electrically insulate adjacent pairs of electrodes: distal signal delivery electrode (16d) and distal sensing electrode (15d); distal sensing electrode (15d) and proximal sensing electrode (15p); proximal sensing electrode (15p) and proximal signal delivery electrode (16p); respectively. The carrier shaft (200) comprises a proximal portion (70), a support tube (90) and a distal portion (50) in serial arrangement.

Referring to FIGS. 2, 4 and 11, four electrical conductors (62), (64), (66) and (68) are provided for servicing the said proximal signal delivery electrode (16p), proximal sensing electrode (15p), distal sensing electrode (15d) and distal signal delivery electrode (16d); respectively. The conductors (62), (64), (66) and (68) are each in the form of an individually insulated conducting element, and are spirally wound in parallel to an external spiral diameter complementary to the diameter of the lumen (74) of a proximal carrier shaft portion (70) into which the resulting spiral windings are press-fitted and glued therein with suitable adhesive. The proximal carrier shaft portion (70) is made from an insulating material such as polyurethane (55D) or silicone for example, and enables the proximal ends of the conductors (62), (64), (66) and (68) to be electrically connected proximally to a suitable controller via suitable proximal connector means, as described hereinbelow. Similarly, the conductors (62), (64), (66) and (68) have suitable distal connector means for operatively connecting each corresponding conductor to said connection means for subsequent connection to the controller, i.e. control unit.

The distal carrier shaft portion (50) comprises four conductors (53) similar to conductors (62), (64), (66) and (68), and are similarly spirally wound in parallel to an external spiral diameter complementary to the diameter of the lumen (54) of distal carrier shaft portion (50) into which the resulting spiral windings are press-fitted and glued using a suitable adhesive. The distal carrier shaft portion (50) is similar to the proximal portion (70) and is made from an insulating material such as polyurethane (55D) or silicone for example. Thus, the proximal portion (70) and distal portion (50) of the carrier shaft (200) have similar flexibilities enabling the latter to be readily inserted into the venous conduits of the body, particularly of the heart, with relative ease.

The distal carrier shaft portion (50) preferably comprises a bend (55) near the typically ogival distal tip (59) thereof, such that the axis (150) of the distal tip (59) is at an angle, typically from about 30° to 90°, and preferably about 45°, to the axis (100) of then rest of the carrier shaft (200) (FIG. 1). As well as helping to maneouvre the device (10) in the vascular system during implantation, this arrangement also helps to anchor the lead in place in a blood vessel after implantation. As the bend (55) is typically deformed or flattened to an angle less than 45°, the resilience of this part of the distal carrier shaft portion (50) presses the bend (55) against the vessel walls, increasing friction and therefore resistance to movement. The tip (59) has a rounded soft distal end (42) to minimize the possibility of damaging blood vessel walls during implantation, and comprises an aperture (58) for enabling the lead to be delivered to the desired implantation site. While many suitable methods exist for delivering, implanting and removing the lead, in the preferred embodiment this is accomplished according to the methods disclosed in co-pending applications filed in the U.S. under U.S. application Ser. No. 09/351, 726 and U.S. Ser. No. 09/317,589, respectively entitled "Catheter with Distal-End Engaging Means" and "A Device and Method for Dragging and Positioning a Member within a Duct in a Body", which are incorporated herein in their entirety be reference thereto. For this purpose, an aperture (44) is formed on said distal portion (59).

Referring to FIGS. 8, 9 and 10 in particular, the distal ends of the conductors (62), (64), (66) and (68) are electrically connected to their respective electrodes via a terminal support tube (90). Terminal support tube (90) is a substantially tubular member made from an insulating material such as polyurethane 75D, for example, having a central lumen (92) extending throughout the length thereof adapted for accommodating a stiffening stylet and enabling its passage therethrough if so desired. The support tube (90) has a cylindrical central section (94) of external diameter approximately equal to the external diameter of the proximal carrier shaft portion (70). A fustroconical proximal plug (92) is comprised at the proximal end of the support tube (90), which comprises an annular step (91) therebetween, the maximum external diameter of the proximal plug (92) being substantially smaller than that of the central section (94). Similarly, a cylindrical distal plug (96) is comprised at the distal end of the support tube (90), which comprises an annular step (95) therebetween, the external diameter of the distal plug (96) being substantially smaller than that of the central section (94). Four longitudinal channels (82), (84), (86) and (88) are formed on the outer surface of the central section (94) for accommodating each the distal end section of a corresponding one of the conductors (62), (64), (66) and (68), and thus comprise a width and depth each substantially equal to or greater than the diameter of said conductors (62), (64), (66) and (68). The channels (82), (84), (86) and (88) are arranged uniformly around the central member (94), and thus adjacent channels are angularly spaced about 90° from one another with respect to the longitudinal axis (100) of the support member (90). The longitudinal extents of the channels (82), (84), (86) and (88) are unequal, each said channel (82), (84), (86) and (88) terminating at a progressively more distal terminal area or base (83), (85), (87) and (89), respectively, along the central section (94). Each said terminal base (83), (85), (87) and (89) comprises a substantially rectangular planar base, having transverse sides corresponding to a chord (c) of depth substantially equal to that of the said channels (82), (84), (86) and (88).

The distal portions (69) of said conductors (62), (64), (66) and (68) are helically wound over the said frusto-conical plug (92), and then the conductors (62), (64), (66) and (68) are separated one from another and axially accommodated in their respective channels (82), (84), (86) and (88), terminating at their respective terminal bases (83), (85), (87) and (89) in which the distal end of each conductor is electrically joined to a corresponding terminal member or plate (73), (75), (77) and (79), respectively. The terminal plates (73), (75), (77) and (79) are substantially prismatic elements in a longitudinal direction, each having a flat inner surface (61) for seating over the corresponding bases (83), (85), (87) and (89) respectively, and an exposed curved upper surface (71) having a curvature similar to that of the cylindrical parts of the central portion (94), as illustrated in FIG. 5, for example. The said exposed surfaces are each substantially larger in area than a transverse cross-sectional area of a corresponding one said at least one conductor, said distal connector means adapted for electrically joining thereto a distal end of a corresponding one said at least one conductor, and said exposed surface adapted for electrically joining thereto a corresponding one of said electrodes.

The terminal plates (73), (75), (77) and (79) are preferably made from Titanium and are joined to the respective distal ends of conductors (62), (64), (66) and (68) by a crimping process, well known in the art.

Referring to FIG. 3, the distal end (72) of said proximal carrier shaft portion (70) comprises an external taper which enables the lumen (74) at this end to stretch and expand over distal portion (69) of the conductors (62), (64), (66) and (68) which has been helically wound over the frusto-conical plug (92) to an external diameter approximately equal to that of the central section (94) or of the carrier shaft (200) itself.

The outer diameter of distal plug (96) may be nominally equal to or slightly smaller than the diameter of the lumen (54) of the distal portion (50), such as to enable the latter to be press-fitted and preferably glued in place with suitable adhesive, with the proximal end of the distal portion (50) in abutting contact with the annular step (95).

In the preferred embodiment, and referring to FIG. 6 in particular, the said proximal and distal sensing electrodes ($15p$) and ($15d$), are substantially identical, each comprising a substantially cylindrical member having an internal diameter slightly greater than the external diameter of the central section (94), i.e., also of the lead (10). Each cylindrical member comprises a longitudinal length preferably less than the external diameter thereof, which is typically less than 1.2 mm. The said sensing electrodes ($15p$) and ($15d$) are slidingly fitted over the central section (94) so that each one of the sensing electrodes ($15p$) and ($15d$) is axially aligned with a corresponding one of the two centrally disposed terminal plates (75), (77). A radial hole (76) extending from the outer cylindrical surface to the bore of each sensing electrodes (15p) and (15d) is aligned with the corresponding terminal plate (75), (77) respectively, and electrical contact between each terminal plate/electrode pair is established by soldering or laser welding the two in each pair via the corresponding radial hole (76).

In the preferred embodiment, and referring in particular to FIG. 12, the proximal and distal delivery electrodes (16p), (16d) each comprise a plurality of, typically 3, electrical conducting elements wound in parallel to a spiral coil-like form having a lumen of diameter slightly larger than the outer diameter of the lead (10). The external diameter of the signal delivery electrodes (16p), (16d) is preferably less than 1.2 mm, and the longitudinal length of each one between 5 mm and about 40 mm, and preferably about 20 mm. The proximal signal delivery electrode (16p) is spirally wound over at least the said distal part (74) of the proximal carrier shaft portion (70) in a distal direction until the windings overlap the most proximally-disposed terminal plate, (73), and these wires of the coils are laser welded thereto to form an electrical connection with corresponding conductor (62). In a similar fashion, the distal delivery electrode (16d) is spirally wound over the said proximal part (57) of the distal portion (50) carrier shaft (200) in a proximal direction until the windings overlap the most distally-disposed terminal plate (79), and these wires of the coils are laser welded thereto to form an electrical connection with corresponding conductor (68).

Referring to FIGS. 1 and 7 in particular, the said non-conducting spacers (52), (54) and (56) each comprise a tube-like element of appropriate axial length to abut an appropriate electrode at each side thereof, and comprise a longitudinal split to enable the spacers (52), (54) (56) to each be aligned on the central section (94) and glued in position thereof with suitable adhesive after the said signal electrodes (15d) and (15p) have been fixed in place.

A lead according to a second embodiment of the invention is illustrated in FIG. 13 and is generally indicated therein at (210). In this embodiment, the elongated shaft (11) includes a proximal section (12) and a distal section (13), and the elongated shaft is made of a plurality of electrical conductors in the form of a circular tube. The proximal end of the shaft is provided with a multi-contact connector (14), through which each conductor is connected to the controller. The distal end of the shaft is provided with a plurality of sensing elements (15) and signal delivery electrodes (16). The sensing electrodes are distributed along the shaft in a way that each sensing electrode resides in close proximity to one or more signal delivery electrodes. The shaft has a central lumen through which a stiff guiding stylet may be inserted. A flexible tip (17) is connected to the distal end of the shaft to minimize blood vessel trauma during lead insertion.

In the second embodiment each sensing element (15) comprises of two sensing electrodes are arranged in pairs. Each pair of electrode is used for bipolar sensing of local electrical activity. Each signal delivery electrode (16) is in close proximity to two pairs of sensing electrode, a pair on each side of the signal delivery electrode. In this configuration, the local electrical activity of cardiac muscle under the signal delivery electrode may be inferred from the measured signals of these two pairs of sensing electrodes.

Figure 17:
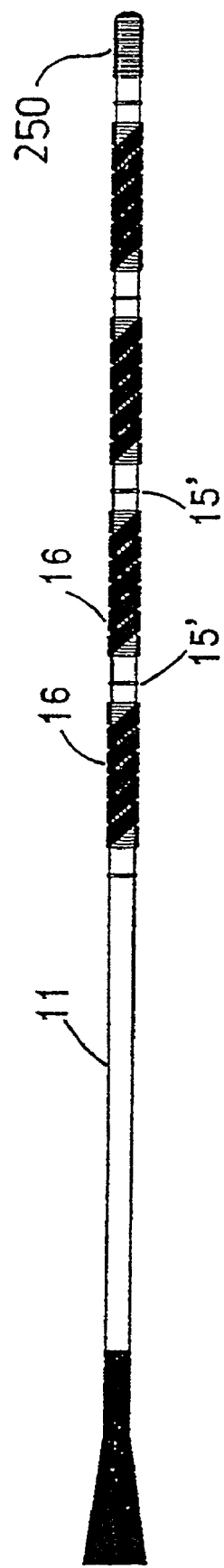
FIG. 17 illustrates in side view the main elements of the third embodiment of the present invention

FIG. 17 illustrates a third embodiment of the invention. Similar to the embodiment illustrated in FIG. 13, each signal delivery electrode (16) is surrounded by two sensing elements (15'). However, in this embodiment each sensing element (15') comprises a single sensing electrode. The electrodes may be used for unipolar sensing and the electrical activity under the signal delivery electrode, which resides between them may be inferred.

Figure 18:
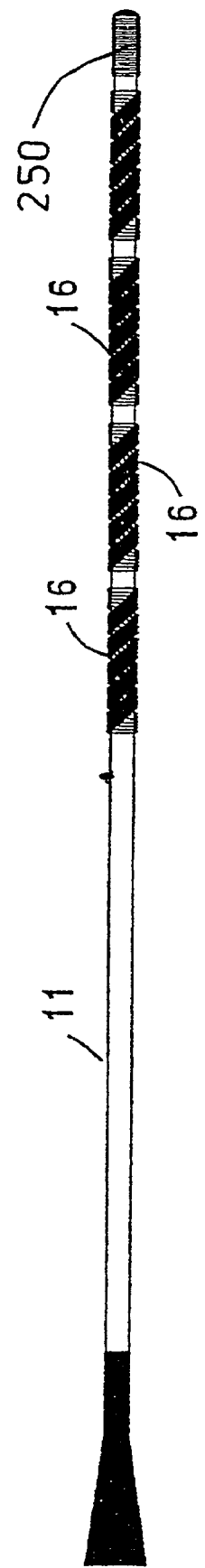
FIG. 18 illustrates in side view the main elements of the fourth embodiment of the present invention.

FIG. 18 illustrates a fourth embodiment of the invention in which there are no separate sensing elements. Bipolar sensing may be accomplished by the signal delivery electrodes (16), which may be used for sensing of localized electrical activity during periods when the electrodes (16) are not used for signal delivery.

Figure 16:
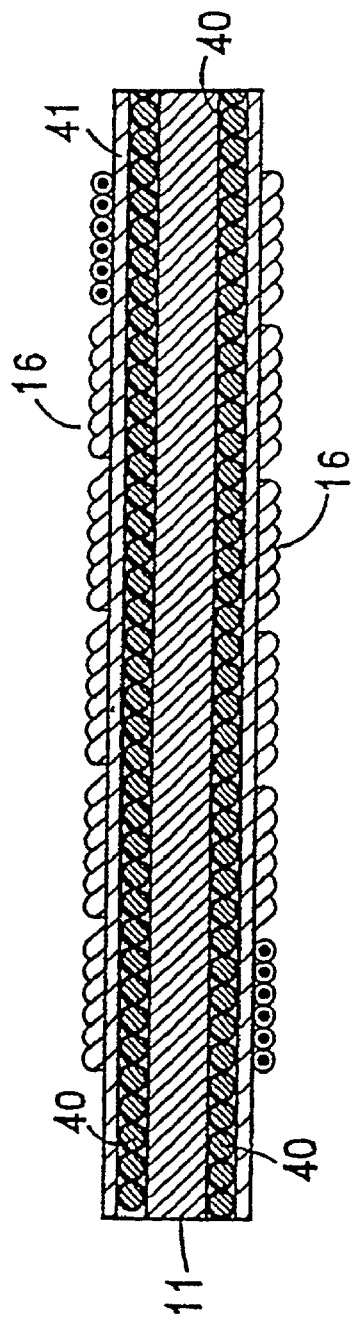
FIG. 16 illustrates in longitudinal cross-sectional view a portion of the embodiment of FIG. 13 taken at the site of a signal delivery electrode.

A cross section of the shaft and a signal delivery electrode (16) of the second, third and fourth embodiments is shown in FIG. 16. In these embodiments, the electrical conductors are arranged in the form of a circular tube with a central lumen. Each conductor (40) is individually insulated and the conductors are twisted together. Additional insulation layer (41), that may be, e.g., a silicone or polyurethane sleeve, covers the twisted conductors. The signal delivery electrode (16), in the form of multi-fillar coil is positioned above the external insulation sleeve. The insulation is removed from one of the insulated conductors and the stimulating electrode is in an electrical contact with that conductor. Each sensing electrode and signal delivery electrode is attached to a different conductor, in a similar manner.

Figure 15B:
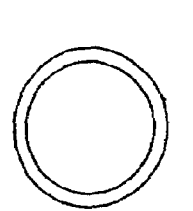
Figure 15A:
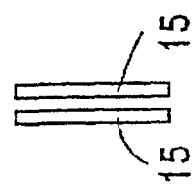
FIG. 15a illustrates in side view the sensing electrodes of the embodiment of FIG. 13.
Figure 14:
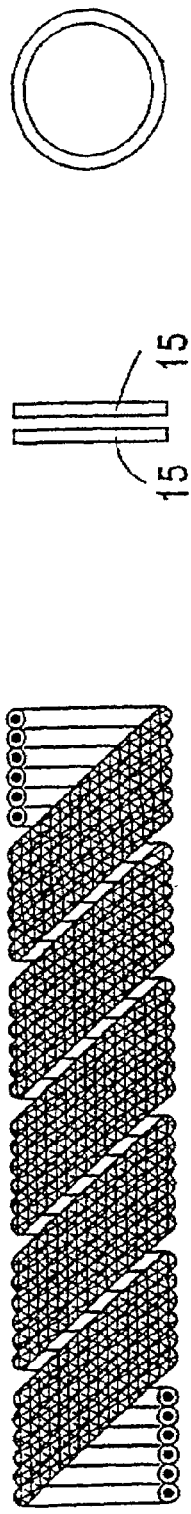
FIG. 14 illustrates in side view the signal delivery electrode of the embodiment of FIG. 13.

In the second, third and fourth embodiments, signal delivery electrodes (16) comprise a hexa-fillar coil which is connected to the control unit through the shaft by at least one conductor. The structure of such hexa-filler electrode is illustrated in FIG. 14. Each sensing electrode (15) (FIG. 13 or 17), in the second or third embodiments, can be constituted by a single ring or by a pair of rings. A transverse cross-section of a sensing electrode is shown in FIG. 15b and a cross-section in the axial plane of the lead of such an electrode constituted by a couple of rings (15) is shown in FIG. 15a.

The distal part of the lead, which is narrow, is to reside in small blood vessels whose inner diameter is less than 1.5 mm and preferably less than 1 mm. In the second, third and fourth embodiments of the invention, the external diameter of the shaft, sensing electrodes and the signal delivery electrodes is less than 1.5 mm and preferably less than 1 mm. The length of the signal delivery electrode, measured longitudinally of the lead, is 20 mm. The length of the lead occupied by the electrodes, as indicated by "a" in FIG. 13, is 100 mm and the length of the lead from the most proximate electrode to the tip of the intrusion head, as indicated by "b" in FIG. 13, is 120 mm.

The distal part comprises multiple sensing and signal delivery electrodes and the proximal part comprises multi-pin connector or IS1 connector, or DF1 connector, or any other suitable connector for delivering the signals of each conductor. In accordance with one embodiment of the invention distance between each signal delivery electrode and a nearby sensing electrode (or electrodes) is between 2-10 mm, preferably 5 mm. The short distance between sensing and signal delivery electrodes allows for accurate monitoring of local electrical activity at a site that is very near to the stimulation site. The inter-signal delivery electrode distance is 3-20 mm, preferably 5 mm.

In all embodiments, the control unit (not shown), which is operatively connected to the lead, includes appropriate circuitry for selecting which pair of electrodes or group of pairs is activated at any given time. The control unit typically includes sources of power, electrical sensors, and control means for controlling the operation of the electrodes, as desired, for the purposes of the device. The sensors are provided for sensing a delivery signal (typically a voltage) transmitted by the sensing electrodes and activating the signal delivery electrode or electrodes that are paired to the sensing electrodes the sensed signal, or lack thereof, indicating what type of stimulus, if any is required to be applied to a given location in the heart. The sensed signal will indicate what kind of stimulus is required, whether a non-excitatory stimulus or a pacing or, exceptionally, a defibrillating stimulus, and the control section will determine what electrical field should be applied via the signal delivery electrodes to produce the stimulus required in each case. Control apparatus for performing these functions are known in the art and need not be described.

The tip (250) of the second, third and fourth embodiments preferably comprise a mechanism (not shown) for attaching it to a guide wire, typically in the form of hollow hole in the tip (250). This hole is used for mounting the lead onto a guide wire and using the guide wire to direct the lead to its final position. Alternatively, the tip (250) may comprise a pair of holes, adjacent to each other in axial arrangement, or diametrically opposed transversely, so that the lead may be threaded on a wire external thereto. In this embodiment, the guide wire is inserted into the GCV and the intrusion head is mounted on the guide wire on its distal hole. Once mounted, the lead is pushed forward (its head sliding on the guide wire) to its final position and the guide wire removed.

Figure 19:
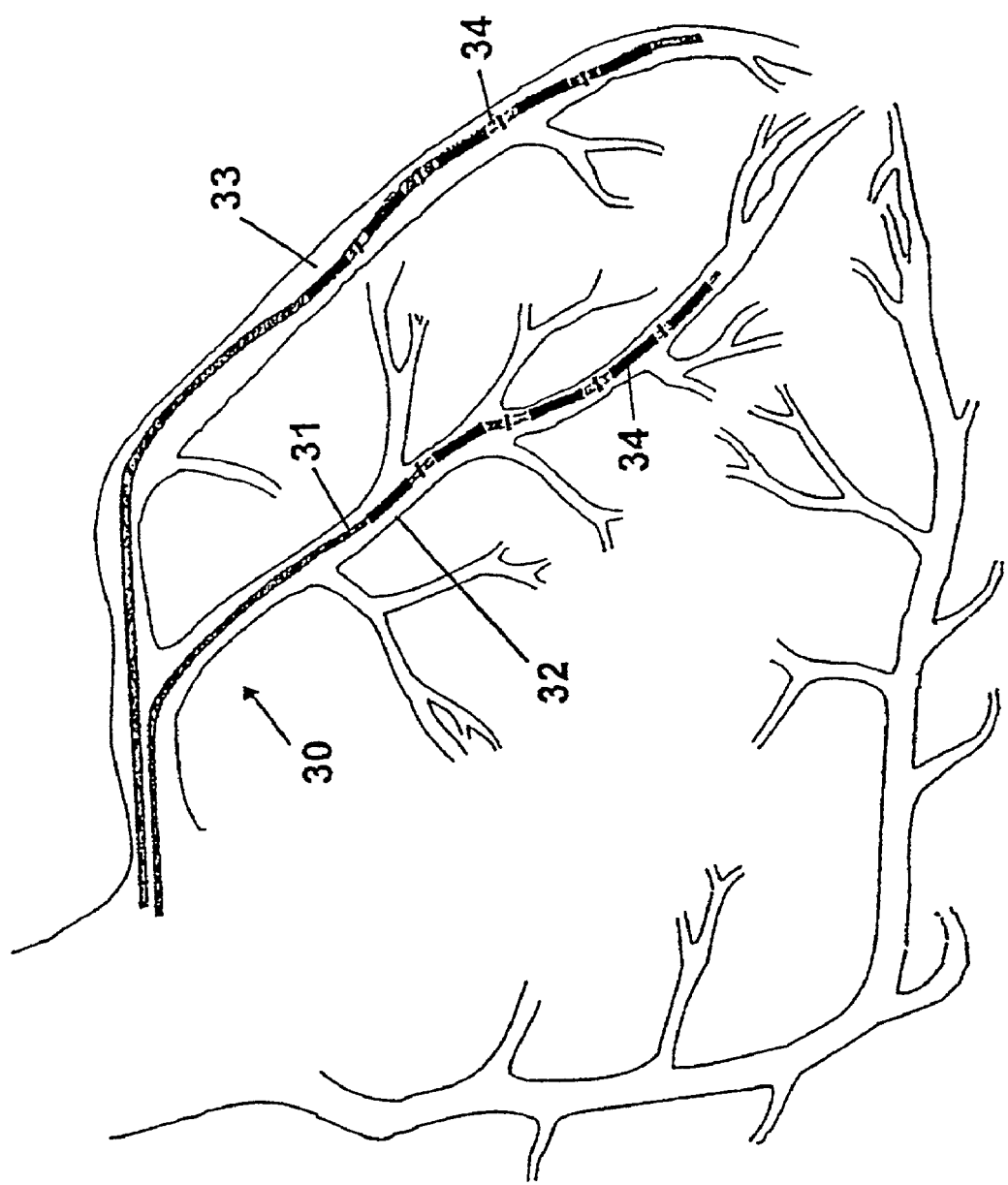
FIG. 19 is a schematic drawing illustrating the positioning of two leads into the coronary vasculature, according to one embodiment of the invention.

FIG. 19 illustrates how the lead may be introduced and implanted in the heart. The lead (10) is introduced into the right atrium via the Vena-cava (superior or inferior) and advanced into the ostium of the coronary sinus (CS), indicated at (30). The lead (31) is pushed further as far as possible into the coronary sinus and up to the great cardiac vein (GCV), indicated at (32), and into the Anterior Interventricular Vein (AIV), indicated at (33). Numeral (34) indicates the sensing electrodes. The introduction into the CS is assisted by introduction of a stylet into the central lumen of the lead up to the distal tip, the lead being typically canted by 30° to 90°, and preferably by about 45°, in its distal part, as described above with respect to the first embodiment, for example. Such stylets and their use are known in the art and need not be illustrated. After placement of the lead in its position, the stylet is removed. The lead attempts to regain its pre-shaped form, thereby creating a mechanical friction between the lead and the wall of the cardiac vein or the CS and thus minimizes the possibility of post implant electrode movements. Alternatively, and particularly for the first embodiment, the implantation is accomplished according to the methods disclosed in co-pending applications filed in the U.S. under U.S. application Ser. No. 09/351,726 and U.S. Ser. No. 09/317,589, respectively entitled "Catheter with Distal-End Engaging Means" and "A Device and Method for Dragging and Positioning a Member within a Duct in a Body".

Figure 20:
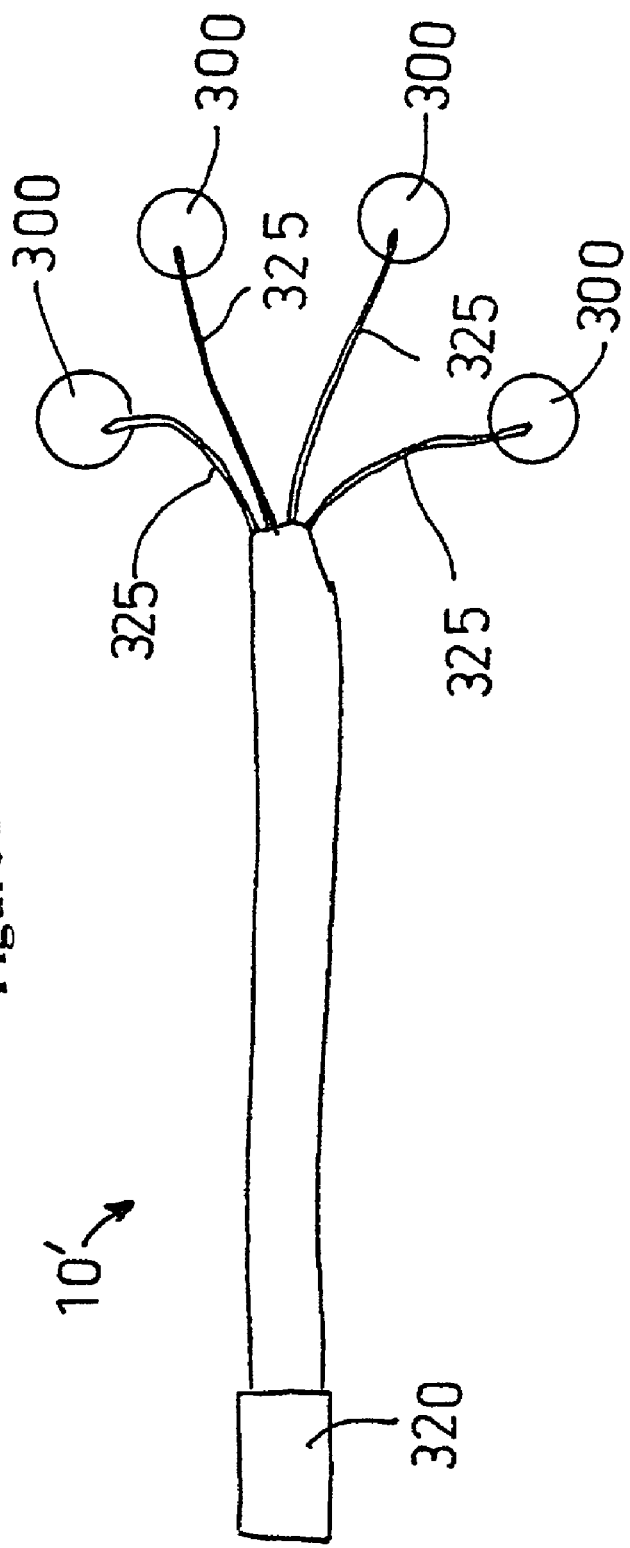
FIG. 20 illustrates in side view the main elements of the fifth embodiment of the present invention.
Figure 21:
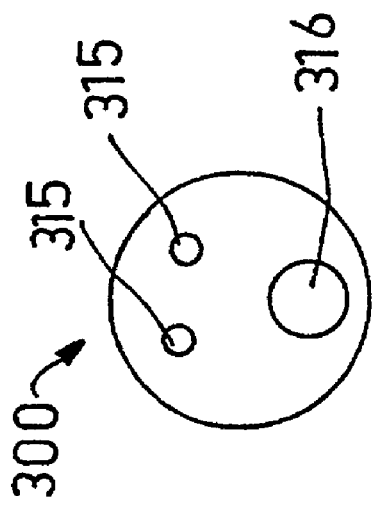
FIG. 21 illustrates in side view the arrangement of electrodes in the electrode unit of the embodiment of FIG. 20.

FIGS. 20 and 21 illustrate a fifth embodiment of the invention particularly adapted for implantation on the epicardial layer of a tissue such as the heart. The lead (10') may comprise one or a plurality, say four for example, of electrode units (300) at the distal end thereof (i.e. the end closest to the portion of tissue which is being treated), each electrode unit typically comprising at one signal delivery electrode (316) and two sensing electrodes (315) in close proximity thereto. Each electrode head (300) may be spatially displaced with the respect to the other heads such as to provide a desired effect on a relatively large area of the tissue. The electrode units (300) are connected to suitable connecting means (320) at the proximal end of the lead (10') via suitable conductors (325) carried by the lead. The lead may be connected to a suitable control unit, similar to that described hereinbefore, also implanted in the body or alternatively located outside the body. The sensing electrodes (315), the signal delivery electrodes (316), and the body of the lead (300) may be made from similar materials as described respectively for the sensing electrodes (15p), (15d), the signal delivery electrodes (16p), (16d) and the shaft (70) as described with reference to the preferred embodiment, mutatis mulandis.

The present invention also relates to a method for applying non-excitatory stimuli to the heart and optionally performing pacing and defibrillation thereof, comprising providing a lead (10) substantially as described herein and positioning said distal portion of the lead within a blood vessel of said heart or portion thereof.

The present invention also relates to a method for applying non-excitatory stimuli to a tissue, comprising providing a lead (10) substantially as described herein, and positioning said distal portion of the lead within a blood vessel of said tissue or portion thereof. Such a method may be applied to any suitable organ of the body or to any body cavity, in particular the heart or a blood vessel or the urinary bladder, or the gastrointestinal system, or the uterus, or the larynx.

The present invention also relates to a method for applying non-excitatory stimuli to the heart and optionally performing pacing and defibrillation thereof, comprising providing a lead (10') substantially as described herein, and positioning said distal portion of the lead on the epicardium of said heart.

The present invention also relates to a method for applying non-excitatory stimuli to said tissue, comprising providing a lead (10') substantially as described herein, and positioning said distal portion of the lead on the epicardial surface of said tissue, in particular wherein said tissue is the cervix, or the uterus, or the urinary bladder.

MODE OF OPERATION

Once placed in its optimal position in the cardiac vein, the lead (10) is used for stimulation of the cardiac muscle that is synchronized with its electrical activity at pre-determined locations. The signal delivery may be synchronized with the intrinsic electrical activity of the cardiac muscle or an ECG or a pacing signal. In most cases, the intrinsic electrical signal arrives to the cardiac muscle via specialized electrical conductance pathways and then propagates in the muscle from one location to its neighbor locations. The appearance of the electrical signal (depolarization of the muscle fibers) does not arrive to the different muscle locations simultaneously, but rather propagates from one location to its neighbor. The arrival of the electrical signal initiates a local mechanical contraction of that specific site. At the same time, nearby sites have not been activated and await the arrival of the electrical signal for the onset of its local mechanical contraction. Since the electrical activity propagates from one location to its neighbor, nearby locations are activated with short delays between them, while remote locations are activated with long delays between them. The delays between neighboring locations may be even longer in pathological tissue (after cardiac infarct and local ischemia).

In order to synchronize the non-excitatory current with the localized intrinsic activity, the sense electrodes are used to deliver the status of local electrical activity to the control unit. The intrinsic electrical activity in every location induces an electrical field in the nearby sense electrodes, which are distributed along the lead, e.g. with an average distance of 25 mm. This induced local electrical field is transmitted to the control unit. Upon detecting this localized electrical activity, the control unit delivers an electrical signal to the non-excitatory signal delivery electrodes that reside near the sense electrodes. Each sensing electrode is preferably constituted not by single ring, but by a couple of rings. The local electrical activity that was detected by the first couple of sense electrodes propagates to nearby muscle locations and induces an electrical field in another couple of sensing electrodes. Again, this localized activity is transmitted to the control unit, and stimulating current is delivered to nearby non-excitatory signal delivery electrodes with pre-defined duration and delay. These non-excitatory signal delivery currents may be independent of each other. The multi-site delivery of non-excitatory signals may be achieved in one or more chambers of the heart, as desired.

Due to the local sensing and signal delivery activity capabilities of the lead, it is also able to inhibit arhythmic events.

The non-excitatory signal delivery electrodes may also function and be used as pacing electrodes. When used for pacing, they can effect all modes of pacing, e.g., single chamber and/or dual chamber and/or multi-chamber (AAI, VVI, DDD etc.). Thus, if for example the intrinsic signal is not detected by the sensing electrodes at the expected time (for example after 1000 msec) the sensing electrode and/or the signal delivery electrodes may be used for the delivery of the pacing signal.

As mentioned above, in addition to the sensing electrodes placed in close proximity to the signal delivery electrodes, more electrodes may be carried by the lead, at any location thereon, the additional electrodes capable of performing sensing functions and/or pacing functions and/or defibrillation functions to enhance the sensing, pacing and defibrillation capabilities of the lead.

Multi site signal delivery within the left ventricle as described above may be combined with pacing and is enabled by the availability of multiple electrodes along the lead stem. However, if some of the electrodes reside in proximity to the atrial wall ("Atrial electrode") while others reside in proximity to the ventricle wall ("Ventricular electrode"), multi-chamber pacing is achieved in the following manner: a pacing signal which is delivered to an "atrial" electrode will evoke an action potential in the atrium, while a pacing signal delivered to the "ventricular" electrode will initiate a ventricular action potential. Each of them may be combined with a non-excitatory signal delivery at each of the sites.

The use of multi-electrode leads enables multi-site signal delivery and multi-chamber pacing employing a single pass lead. This type of single pass, multi-chamber pacing can be continuous or originate on demand. In order to achieve this single pass, multi-chamber signal delivery via the lead, each electrode has to be identified as "atrial" or "ventricular". The "ventricular" electrodes may be used for ventricular pacing and multi-site signal delivery. The determination of the location is done by sensing the electrical activity from each electrode. Once the lead is positioned in the GCV, the distal electrodes will exhibit electrical signals from the left ventricle, while the proximal electrodes exhibit electrical signals from the left atrium. By monitoring the electrical activity from the different electrodes, the position of an anatomical border between the atrium and the ventricle can be identified through the sensed electrical signals.

In tests carried out on an anaesthetised canine model, the same lead was used for dual-chamber pacing and for the application of non-excitatory electrical signals to localized regions of the left ventricle in the following way: the lead comprises 8 electrodes, #1 to #8, #1 being the most distal electrode and #8 being the most proximal electrode. The distal portion of the lead was positioned in the GCV while its proximal part resided in the coronary sinus. We mapped the electrical activity recorded from the different electrodes after inserting the lead to its final position and found that the anatomical border between the ventricle and the atrium resided between electrodes #4 and #5. We used electrode #8 (most proximal electrode) for atrial pacing, and electrode #3 for ventricular pacing. Once paced, we applied the non-excitatory electrical signals via electrodes 1 and 4 that were located on the left ventricle, which were synchronized to the locally sensed electrical depolarization. FIG. 22(a) illustrates the non-excitatory signal (ETC) applied via the signal delivery electrodes with respect to time (T), while FIG. 22(b) shows the measured pulsative flow (P) in the aorta vs. time (T), the correlated improvement being evident.

A conduit may be provided in the lead for local delivery of drugs, e.g. steroids, at different locations along the shaft. This element is not illustrated, as it is known in the art for other leads. Such a conduit may also be used for passage of a guide wire therethrough during positioning of the lead or lead, using an "over-the-wire" technique, which is known in the art.

As will be apparent to the skilled person, the electrode of the invention can, with the necessary shape modifications, be used both epicardially and in a heart chamber, and its use is not limited to a specific location. Additionally, the lead of the invention is not limited to its use within the heart, and it can be employed to sense the activity of, and to deliver stimuli to, a variety of other organs and body cavities, including—but not limited to—the urinary bladder, the gastrointestinal system, the uterus, the larynx, and blood vessels.

While some embodiments of the invention have been described by way of illustration, it will be apparent that many modifications, variations and adaptations may be carried out by persons skilled in the art without departing from its spirit or exceeding the scope of the claims.

The invention claimed is:

1. A lead for modifying the activity of at least a portion of a tissue, said lead comprising:
   at least one signal delivery electrode in the form of a flexible circumferential element positioned around the lead, having a diameter less than 1.5 mm, and having capacitance greater than 300 microfarads and less than 3000 microfarads, wherein the electrode is adapted to withstand chronic delivery to said at least portion of tissue a non-excitatory electric field having an amplitude and duration suitable to modify the contractility of a human cardiac muscle when applied during a refractory period of said muscle; and
   a connector adapted to connect to said at least one signal delivery electrode for enabling said at least one signal delivery electrode to be operatively connected to control circuitry.

2. A lead according to claim 1, wherein the at least one signal delivery electrode is made from a material selected from titanium coated with iridium oxide.

3. A lead as claimed in claim 1, wherein at least one of the at least one signal delivery electrodes is a unitary electrode also adapted for sensing activity of said at least portion of a tissue and providing a signal characteristic of said activity.

4. A lead as claimed in claim 1, further compromising control circuitry, wherein the control circuitry is characterized in being adapted for either selectively enabling a non-excitatory electric field to be generated by said at least one signal delivery electrode such as to modify the contractility of a human cardiac muscle when applied during a refractory period of said muscle or for selectively not generating an electric field wherein said electric field is either generated or not generated according to at least one characterizing feature of the signal previously provided by the same or another one of said at least one sensing electrode.

5. A lead according to claim 1, wherein the distal end of said lead is flexible enough to be mounted on and conform to a cardiac chamber wall.

6. A lead according to claim 1, wherein the external diameter of said lead is smaller than the inner diameter of a human coronary sinus, thereby enabling said lead to pass through said coronary sinus.

7. A lead according to claim 1, wherein the external diameter of said lead is smaller than 1.5 mm.

8. A lead according to claim 1, wherein the external diameter of said signal deliver electrode is smaller than 1.2 mm.

9. A lead according to claim 1, wherein the external diameter and flexibility of said lead are suitable for insertion through the human coronary sinus reaching branches located on the left ventricle free wall.

10. A lead according to claim 1, wherein the at least one signal delivery electrode is longer than the length of an implantable chronic pacing electrode and shorter than the length of an implantable defibrillation electrode.

11. A lead according to claim 1, wherein the at least one signal delivery electrode is longer than 10 mm and shorter than 40 mm.

12. A lead according to claim 1, wherein the at least one signal delivery electrode has impedance higher than 50 Ohm and lower than 500 Ohm.

13. A lead according to claim 1, further comprising:
at least one sensing electrode flanking said at least one signal delivery electrode adapted for sensing the activity of said at least portion of a tissue and providing a signal characteristic of said activity; and
second connector operatively connected to said at least one sensing electrode for enabling said at least one sensing electrode to be operatively connected to a suitable circuitry for determining a stimulus to be applied by said at least one signal delivery electrode.

14. A lead according to claim 13, wherein the at least one sensing electrode includes pairs of sensing electrodes.

15. A lead according to claim 14, wherein a pair of sensing electrodes from the pairs of sensing electrodes is positioned on each side of the at least one signal delivery electrode.

16. A lead according to claim 15, wherein the pairs of sensing electrodes are positioned on the lead in a position so that they can sense a local electrical activity of cardiac muscle under the at least one signal delivery electrode.

17. A lead according to claim 1, wherein said at least one signal delivery electrode is made from titanium coated with titanium nitride.

18. A lead according to claim 1, wherein said at least one signal delivery electrode is made from platinum iridium coated with iridium oxide.

19. A lead according to claim 1, wherein said at least one signal delivery electrode is made from platinum iridium coated with titanium nitride.

20. A lead according to claim 1, wherein said at least one signal delivery electrode is made from platinum iridium coated with sintered platinum.

21. A lead according to claim 1, wherein said at least one signal delivery electrode is made from titanium.

22. A lead according to claim 1, wherein said at least one signal delivery electrode is made from platinum iridium.

23. A lead according to claim 1, wherein said at least one signal delivery electrode is made from pyrolitic carbon.

24. A lead according to claim 1, wherein said at least one signal delivery electrode is made from any conductive material approved for chronic use in the body.

25. A lead according to claim 1, wherein the at least one signal delivery electrode is formed by a coil and wherein the coil is spirally wound around the lead.

26. A lead according to claim 1, wherein the at least one signal delivery electrode is formed by a mesh of wires.

27. A lead according to claim 1, wherein the lead includes a proximal end and a distal end with a tip, and wherein the tip of the distal end is a soft rounded tip.

28. A lead according to claim 27 comprising a bend at the distal end, wherein the bend is at an angle between 30 degree to 90 degree.

29. A lead according to claim 1 wherein the at least one signal delivery electrode further comprises a plurality of signal delivery electrodes, and wherein the plurality of signal delivery electrodes are spaced along the lead such as to occupy a lead length of between about 20 mm and about 150 mm.

30. A lead according to claim 29 wherein a distance between adjacent pairs of the electrodes is between about 5 mm to 30 mm.

* * * * *